United States Patent
Berger et al.

(10) Patent No.: US 6,190,612 B1
(45) Date of Patent: Feb. 20, 2001

(54) OXYGEN SENSING MEMBRANES AND METHODS OF MAKING SAME

(75) Inventors: Joseph Berger, Muttenz (CH); Thomas C. Collins, Milford; Rudolf E. Slovacek, Norfolk, both of MA (US)

(73) Assignees: Bayer Corporation, East Walpole, MA (US); Novartis AG, Basel (CH)

( * ) Notice: Under 35 U.S.C. 154(b), the term of this patent shall be extended for 0 days.

(21) Appl. No.: 09/010,161

(22) Filed: Jan. 21, 1998

(51) Int. Cl.$^7$ .................................................. G01N 21/64
(52) U.S. Cl. ........................................... 422/82.07; 436/68
(58) Field of Search .............................. 422/82.06, 82.07, 422/82.08; 436/68, 172, 136, 138

(56) References Cited

U.S. PATENT DOCUMENTS

| | | |
|---|---|---|
| 2,761,417 | 9/1956 | Russell et al. ........................ 118/410 |
| 3,992,158 | 11/1976 | Przybylowicz et al. . |

(List continued on next page.)

FOREIGN PATENT DOCUMENTS

| | | |
|---|---|---|
| 0105870 | 10/1983 | (EP) . |
| 0119861 | 11/1987 | (EP) . |
| 0409033 | 7/1990 | (EP) . |
| 0442276 | 1/1991 | (EP) . |
| 0142849 | 8/1992 | (EP) . |
| 0287328 | 10/1993 | (EP) . |
| 0287327 | 7/1994 | (EP) . |
| 87/00023 | 1/1987 | (WO) . |
| 90/07107 | 6/1990 | (WO) . |
| 92/19957 | 11/1992 | (WO) . |
| 95/10522 | 4/1995 | (WO) . |
| 95/26501 | 10/1995 | (WO) . |
| 95/30148 | 11/1995 | (WO) . |
| 97/37210 | 10/1997 | (WO) . |

OTHER PUBLICATIONS

Klimant, I. et al, "Oxygen–Sensitive Luminescent Materials Based on Silicone–Soluble Ruthenium Diimine Complexes" Analytical Chemistry, vol. 67, No. 18, pp. 3160–3166, Sep. 1995.*

Aartsma, T. et al., "Porphyrins.43. Triplet Sublevel Emission of Platinum Tetrabenzoporphyrin by Spectrothermal Principal Component Decomposition"; *J.Am.Chem. Soc.* 104, pp. 6278–6283 (1982).

Brandrup, J. et al., "Permeability and Diffusion Data" Polymer Handbook, 3rd edition, pp. VI/435–VI/449, John Wiley and Sons, New York, NY (1989).

(List continued on next page.)

Primary Examiner—Jeffrey Snay
(74) Attorney, Agent, or Firm—Dianne E. Reed; Louis L. Wu; Reed & Associates

(57) ABSTRACT

Optical sensor formulations comprising polymeric sensing formulations and methods of predictably making optical sensor formulations, for, e.g., measuring $O_2$ levels in patient blood samples. These formulations may be, e.g., deposited as a membrane on light-transmissive substrates. In an embodiment, $O_2$-sensing formulations may be made by a process including selecting a first homopolymer comprised of first monomeric units, the first homopolymer having a first $Perm_{O2}$ value; selecting a second homopolymer comprised of second monomeric units, the second homopolymer having a second $Perm_{O2}$ value that is different from the first $Perm_{O2}$ value; and copolymerizing the first and second monomeric units to obtain a copolymer having an intermediate $Perm_{O2}$ value, i.e., between the two $Perm_{O2}$ values, the intermediate $Perm_{O2}$ providing the desired $Perm_{O2}$ for the desired oxygen sensing formulation. By adjusting the relative amounts of the first and second monomeric units, a series of polymers having a desired range of intermediate permeability values (and hence Stem-Volmer characteristic $k_{SV}$ values) may be obtained.

28 Claims, 8 Drawing Sheets

U.S. PATENT DOCUMENTS

| | | |
|---|---|---|
| 4,003,707 | 1/1977 | Lübbers et al. . |
| 4,042,335 | 8/1977 | Clément . |
| 4,356,149 | 10/1982 | Kitajima et al. ............... 422/56 |
| 4,476,870 | 10/1984 | Peterson et al. ............ 128/634 |
| 4,587,101 | 5/1986 | Marsoner et al. ............ 422/56 |
| 4,645,744 | 2/1987 | Charlton et al. ............. 436/74 |
| 4,649,123 | 3/1987 | Charlton et al. ............. 436/79 |
| 4,670,218 | 6/1987 | Gantzer et al. .............. 422/56 |
| 4,680,268 | 7/1987 | Clark, Jr. .................... 435/291 |
| 4,689,309 | 8/1987 | Jones ............................ 436/95 |
| 4,716,363 | 12/1987 | Dukes et al. ................. 324/77 |
| 4,734,375 | 3/1988 | Charlton ....................... 436/74 |
| 4,752,115 | 6/1988 | Murray, Jr. et al. ......... 350/96.29 |
| 4,781,890 | 11/1988 | Arai et al. .................... 422/56 |
| 4,810,655 | 3/1989 | Khalil et al. ................ 436/138 |
| 4,824,789 | 4/1989 | Yafuso et al. ............... 436/68 |
| 4,857,472 | 8/1989 | Wolfbeis ..................... 436/122 |
| 4,861,727 | 8/1989 | Hauenstein et al. ........ 436/136 |
| 4,895,156 | 1/1990 | Schulze ....................... 128/634 |
| 4,895,704 | 1/1990 | Arai et al. .................... 422/57 |
| 4,919,891 | 4/1990 | Yafuso et al. ............... 422/58 |
| 4,925,268 * | 5/1990 | Iyer et al. ................... 350/96.29 |
| 4,974,929 | 12/1990 | Curry ........................... 350/96.29 |
| 5,028,395 * | 7/1991 | Sebille et al. ............... 422/82.06 |
| 5,030,420 | 7/1991 | Bacon et al. ................ 422/82.07 |
| 5,043,286 | 8/1991 | Khalil et al. ................ 436/136 |
| 5,047,350 | 9/1991 | Switalski et al. ........... 436/136 |
| 5,075,127 | 12/1991 | Yafuso et al. ............... 427/2 |
| 5,081,041 | 1/1992 | Yafuso et al. ............... 436/68 |
| 5,081,042 | 1/1992 | Yafuso et al. ............... 436/68 |
| 5,091,800 | 2/1992 | Offenbacher et al. ...... 359/350 |
| 5,127,405 | 7/1992 | Alcala et al. ................ 128/633 |
| 5,173,432 | 12/1992 | Lefkowitz et al. .......... 436/138 |
| 5,190,729 | 3/1993 | Hauenstein et al. ........ 422/91 |
| 5,208,147 | 5/1993 | Kagenow et al. ........... 435/14 |
| 5,266,271 * | 11/1993 | Bankert et al. .............. 422/82.07 |
| 5,281,825 | 1/1994 | Berndt et al. ................ 250/458.1 |
| 5,298,144 | 3/1994 | Spokane ....................... 204/403 |
| 5,326,531 | 7/1994 | Hahn et al. .................. 422/82.06 |
| 5,341,805 | 8/1994 | Stavridi et al. .............. 128/633 |
| 5,352,348 | 10/1994 | Young et al. ................ 204/153.12 |
| 5,387,329 | 2/1995 | Foos et al. ................... 204/415 |
| 5,387,525 | 2/1995 | Munkholm ................... 436/111 |
| 5,453,248 | 9/1995 | Olstein ......................... 422/82.07 |
| 5,462,858 | 10/1995 | Oenick et al. ............... 435/16 |
| 5,462,879 | 10/1995 | Bentsen ........................ 436/136 |
| 5,464,777 | 11/1995 | Yip ............................... 436/98 |
| 5,494,562 | 2/1996 | Maley et al. ................. 204/403 |
| 5,506,148 | 4/1996 | Munkholm ................... 436/111 |
| 5,520,883 | 5/1996 | Charlton et al. ............. 422/56 |
| 5,536,664 * | 7/1996 | Switalski et al. ........... 436/171 |
| 5,601,694 | 2/1997 | Maley et al. ................. 204/415 |
| 5,605,152 | 2/1997 | Slate et al. ................... 128/634 |
| 5,607,644 * | 3/1997 | Olstein et al. ............... 422/82.07 |
| 5,624,847 | 4/1997 | Lakowicz et al. ........... 436/68 |
| 5,631,340 | 5/1997 | Olstein ......................... 528/59 |
| 5,640,470 * | 6/1997 | Iyer et al. ..................... 385/12 |

OTHER PUBLICATIONS

Bruno, et al. "All–Solid–State Miniaturized Fluorescence Sensor Array for the Determination of Critical Gases and Electrolytes in Blood" *Anal. Chem.* 69, pp. 507–513 (1997).

Demas, J. et al., "Design and Applications of Highly Luminescent Transition Metal Complexes"; *Analytical Chemistry,* vol. 63, No. 17; pp. 829–837 (1991).

Kautsky, V. et al., "Nachweis geringster Sauerstoffmengen durch Phosphoresztenzilgung", *Zeitschrift fir anorganische und allgemeine chemie. Band* 222, pp. 126–134 (1935). (German).

Kautsky, V. et al., *"Luminescenzumwandlung durch Sauerstoff Nachweis geringster Sauerstoffmengen", Zeitschrift Naturforschung* 2a, pp. 167–172 (1947). (German).

Klimant, I. et al., "Oxygen–Sensitive Luminescent Materials Based on Silicone–Soluble Ruthenium Diimine Complexes" *Anal. Chem.* 67 pp. 3160–3166 (1995).

Lui, Hsue–Yang et al., "Oxygen Permeability of Sol–Gel Coatings", *Applied Spectroscopy,* vol. 46, No. 8 pp.1266–1272 (1992).

MacCraith et al., "Optical Chemical Sensors Based on Sol–Gel Materials: Recent Advances and Critical Issues", J. Sol–Gel Sci. and Tech., vol. 8, pp. 1053–1061 (1997).

Papkovsky et al., "Phosphorescent Complexes of Porphyrin Ketones: Optical Properties and Application to Oxygen Sensing", *Anal. Chem.* 67, pp. 4112–4117 (1995).

Papkovsky et al., "Phosphorescent Polymer Films for Optical Oxygen Sensors", *Biosensors & Electronics* 7, pp. 199–206 (1991).

Roffey, "Photopolymerization of Surface Coatings", *Wiley–Interscience,* p. 100–117 (1985).

Salame, M. "Transport Properties of Nitrile Polymers", J. Polymer Sci. Symp. 41, pp. 1–15 (1973).

Stern, V. et al., "Uber die Abklingungszeit der Fluoreszenz", *Physik. Zeitschr.* XX; pp. 183–188 (1919). (German).

Vinogradov et al., "Metallotetrabenzoporhyrins. New Phosphorescence Probes for Oxygen Measurements", *J. Chem. Soc. Perkin Trans.* 2, pp. 103–111 (1995).

Watts, R.J. et al., "Spectroscopic Characterization of Complexes of Ruthenium (II) and Iridium (III) with 4,4'–biphenyl–2,2'–dipyridine and 4,7–Diphenyl–1,10–phenanthroline", *J. Am. Chem. Soc.* 93, pp. 3184–3188 (1971).

Yang et al., "Oxygen Permeability Coefficients of Polymers for Hard and Soft Contact Lens Applications",*J. Membrane Sci.* 9, pp. 53–67 (1981).

* cited by examiner

OXYGEN PERMEABILITY MEASUREMENTS:
LIQUID/MEMBRANE/LIQUID CONFIGURATION

OXYGEN SENSING MEMBRANES AND METHODS OF MAKING SAME

BACKGROUND OF THE INVENTION

The present invention relates generally to polymeric sensing membranes, and more particularly to polymeric sensing membranes comprising luminescent dyes and polymeric matrices having predictable gas permeabilities, and methods of making these membranes.

The ability to monitor gas concentration is advantageous in a variety of situations. For example, reactions carried out on a large scale in the chemical industry, such as fermentation reactions, often require the measurement of certain reactant or product gases. In medical care, continuous monitoring of the respiratory gases is becoming a common procedure for the study of respiration, assisting in anesthesiology and the treatment and diagnosis of cardiopulmonary disorders. In particular, it is often desirable to be able to monitor the level of oxygen in blood using in vitro methods.

One approach to measuring oxygen levels in blood is to use an oxygen-sensitive luminescent membrane. Such membranes typically comprise a polymeric matrix material and luminescent dye molecules dispersed within the polymeric material. The luminescent molecules are capable of emitting fluorescence or phosphorescence from excited electronic states which can be collisionally quenched by molecular oxygen. This process is commonly known as Stern-Volmer quenching and is described by the relationship $$F_0/F = \tau_0/\tau = 1 + \tau_0 \cdot k_q[O_2] \tag{1}$$

where $F_0$ and $\tau_0$ are the luminous intensity and the relaxation time for the luminescent dye in the absence of molecular oxygen, $F$ and $\tau$ are the luminous intensity and the relaxation time when the molecular oxygen concentration $[O_2]$ is greater than zero, and $k_q$ is the quenching constant for the luminescent dye molecule. This equation is often rewritten in the form $$F_0/F = \tau_0/\tau = 1 + k_{SV} \cdot pO_2 \tag{2}$$

where $k_{SV}$ is the Stern-Volmer constant (in $(\text{mmHg})^{-1}$ or $\text{torr}^{-1}$) and $pO_2$ is the partial pressure of oxygen. For the application described here, partial pressures are given in units of mmHg where one mmHg is equivalent to one torr.

In use, oxygen-sensitive membranes are exposed to electromagnetic radiation capable of exciting the luminescent dye molecule from the ground electronic state to an excited electronic state. This usually involves the excited singlet state for fluorescent molecules or the longer lived triplet state for phosphorescent dye molecules. When the luminescent dye molecules undergo a transition from the excited electronic state back to the ground state, a photon is emitted at a characteristic wavelength. The amount of oxygen in blood can be determined by measuring a change in the luminescent state of dye molecules, since the decay rate from the excited state is altered by the presence or absence of oxygen gas.

Several different techniques exist which are designed to measure the emission properties of luminescent dye molecules dispersed within a matrix or polymeric materials. For example, one can adapt a relatively simple approach of measuring the fluorescence intensity elicited by a constant excitation source, e.g., as disclosed in U.S. Pat. No. 4,476,870. U.S. Pat. Nos. 4,810,655 and 4,895,156 further disclose methods of measuring the time resolved emission of a luminescent dye molecule dispersed within a polymeric material. If a pulse of light, used to excite a dye molecule, is of a relatively short duration ($t \ll \tau$), the decay of emission intensity from the initial value $F_i$ will be approximately described by $$F(t) = F_i \cdot e^{-t/\tau} \tag{3}$$

Various sampling and regression schemes can be used to estimate a value for $\tau$.

As disclosed in U.S. Pat. Nos. 5,127,405, 5,281,825, and WO Application No. 92/19957, measurement of the phase shift for luminescence emitted by a luminescent dye molecule may be accomplished using a modulated excitation source. The excitation signal can be modulated such that the source intensity varies sinusoidally $$E(t) = E_p \cdot \left(\frac{1 + \sin \omega t}{2}\right) \tag{4}$$

where $E_p$ is the peak excitation source intensity and $\omega$ is the angular frequency of the excitation signal. The luminescence emission signal $F(t)$ from the dye will also vary sinusoidally at the same frequency as the excitation signal, except with a phase lag which is related to the relaxation time by $$F(t) = \frac{1}{(1 - \omega\tau^2)^{1/2}} \cdot F_p \cdot \left(\frac{1 + \sin(\omega t - \phi)}{2}\right) \tag{5}$$

where $F_p$ is the luminescence intensity that would result from a constant excitation at intensity $E_p$ and $\Phi$ is the phase lag. The relaxation time can be calculated from the observed phase lag using the equation $$\tau = \frac{1}{\omega} \cdot \tan \phi \tag{6}$$

Also, as disclosed in, e.g., U.S. Pat. No. 4,716,363 and WO application No. 90/07107, a constant phase method for extracting relaxation information from samples may be employed through the use of a variable frequency modulated source. This constant phase technique includes adjusting the frequency (f) of the modulated excitation source with a feedback loop so that a constant phase lag, preferably in the range of 45°, is maintained. A rearrangement of equation (6) and substitution of $\omega = 2\pi f$ yields:

$$f = \tan \phi/(2\pi\tau) \tag{7}$$

If $\phi$ is held constant at 45°, then $\tan \phi = 1$, and by substituting $\tau$ from equation (2), it can be shown that:

$$f = (1 + k_{SV} \cdot pO_2)/2\pi\tau_o \tag{8}$$

Thus, the operating frequency of the feedback loop is directly proportional to the partial pressure of oxygen; as such, the constant phase method provides several advantages over the time resolved and constant frequency methods. For example, the constant phase method significantly reduces the complexity of the calculations required to produce a reported result. In addition, maintaining a constant phase lag permits the phase detector to operate in the most sensitive part of the response curve and optimizes signal to noise ratios by maintaining a constant signal amplitude over a wide range of oxygen partial pressures.

The time resolved, phase shift or frequency modulation methods are all advantageous particularly for the measurement of samples such as blood or milk; the light scattering characteristic of these samples will not affect the apparent quenching constants for the luminescence. However, while these methods may eliminate the need for optically opaque cover membranes to reduce optical interference of simple fluorescence amplitude-based measurements (such as disclosed in U.S. Pat. Nos. 4,919,891; 5,081,041, and 5,091,800), the instrumentation needed to perform such relaxation-based measurements is decidedly more complex.

Different luminescent dye/polymeric material combinations have been employed to make oxygen sensing membranes. For example, U.S. Pat. Nos. 4,003,707 and 4,476,870 disclose the use of near-UV absorbing dyes from the pyrene and pyrelene families, respectively. U.S. Pat. Nos. 4,587,101; 4,752,115; 5,030,420, and 5,631,340 advocate the use of ruthenium complexes which undergo Stern-Volmer quenching by oxygen and have longer lived excited states, as outlined in *Anal. Chem.* 63,337 (1991). Lanthanide complexes, which also have longer lifetimes, have also been used for oxygen sensing purposes, e.g., U.S. Pat. No. 4,861,727. Other luminescent dye molecules, such as porphyrin derivatives, are disclosed in U.S. Pat. No. 5,043,286 and WO application No. 95/10522, as well as in *Biosensors and Bioelectronics* 7, 199 (1991), *Anal. Chem.* 67, 4112 (1995), and *J. Chem. Soc. Perkin Trans.* 2, 103 (1995).

Polymeric matrix materials which have been used include those disclosed in U.S. Pat. Nos. 4,587,101; 4,752,115 and 5,043,286, teaching that unplasticized polymers or untreated sol-gels (e.g., U.S. Pat. No. 5,047,350) offer relatively poor performance when used in dye-based gas sensing membranes. At the same time, plasticized membranes or additives are likewise disadvantageous, since plasticizers and additives can leach out and affect oxygen permeability over time and under various storage conditions. U.S. Pat. No. 4,476,870 further discloses that oxygen sensing membranes having low oxygen permeable membranes are relatively insensitive. One response to poor performance or undesirable Stern-Volmer response is shown in U.S. Pat. No. 5,462,879, wherein a second dye with a different quenching constant was added to the polymer/dye membrane formulation.

Previous teachings regarding selecting appropriate polymeric materials and luminescent dye molecules for particular sensing membrane applications are sparse, and there has been only limited success in producing a reliable membrane having the specific response characteristic desired. As such, sensing membranes have been made with available polymeric materials and luminescent dye molecules using a more or less empirical or trial-and-error method, i.e., polymeric sensing membranes incorporating dye molecules having a known relaxation time $\tau$ are made, then tested to see if a membrane having the desired properties (Stern-Volmer response or $k_{SV}$) was obtained. Thus, the sensitivity of a particular polymeric sensing membrane for a given combination of materials has only been determined after the fact. If the desired performance was not obtained, the practice of adding high amounts of plasticizers, (as taught in U.S. Pat. Nos. 4,587,101; 4,752,115 and 5,043,286), was performed to adjust the membrane properties. As a result, known polymeric sensing membranes require relatively complex and expensive equipment, offer relatively poor sensitivity or both.

In co-pending and commonly owned U.S. patent application Ser. No. 08/617,714, the entire disclosure of which is incorporated herein by reference, methods for choosing a dye and polymer combination which gives a desired response over a given dynamic range of $pO_2$ values are disclosed, and properties of dyes and polymers or heteropolymers which, when combined, result in membranes having desired oxygen sensing properties, are also disclosed. The method is based on experimental support for the finding that the Stern-Volmer constant of a polymeric sensing membrane is mathematically related to the relaxation time of the luminescent dye molecule and the oxygen permeability of the polymeric material in which the dye is dispersed. In particular, the Stern-Volmer constant may be given as:

$$k_{SV} = 4\pi \cdot N_A \cdot P \cdot \tau_o \cdot \text{Perm}_{O2} \tag{9}$$

where $N_A$ is Avogadro's number, p is the relative likelihood of an oxygen molecule colliding with a dye in an electronically excited state and $\text{Perm}_{O2}$ is the permeability of the polymeric material. However, predictably determining suitable polymers having a desired range of $O_2$ permeabilities for incorporation in oxygen sensing membranes heretofore has been lacking.

SUMMARY OF THE INVENTION

The present invention responds to the need in the art for easier and more efficient methods of making optical sensor formulations comprising a luminescent dye and a polymeric matrix, as well as the sensors that may be made by such methods. The invention responds to this need by providing, in an embodiment, methods for making light-transmissive, oxygen-permeable matrix materials which desirably have a range of oxygen permeabilities ($\text{Perm}_{O2}$), which in turn provide oxygen sensing compositions having Stern-Volmer constants in a desired range. Preferably, the process includes selecting a first homopolymer comprised of first monomeric units, the first homopolymer having a first $\text{Perm}_{O2}$ value; selecting a second homopolymer comprised of second monomeric units, the second homopolymer having a second $\text{Perm}_{O2}$ value that is higher than the first $\text{Perm}_{O2}$ value; and copolymerizing the first and second monomeric units to obtain a copolymer having an intermediate $\text{Perm}_{O2}$ value, i.e., between the two $\text{Perm}_{O2}$ values, the intermediate $\text{Perm}_{O2}$ providing the desired $\text{Perm}_{O2}$ for the desired oxygen sensing formulation.

Another embodiment includes selecting the first and second homopolymers and preparing (using varying ratios of the first and second monomeric unit reactants) a range of copolymers having a range of $\text{Perm}_{O2}$ values. From this range of $\text{Perm}_{O2}$ values a homopolymer reactant ratio for a given reaction which results in a desired $\text{Perm}_{O2}$ may be determined, e.g., by plotting a curve of $\text{Perm}_{O2}$ v. homopolymer ratio.

Yet another embodiment relates to optical sensors comprising the copolymers disclosed herein which contain luminescent dyes. In one embodiment, the luminescent material is a fluorescent material. In another embodiment, the luminescent material is a phosphorescent material. In a further embodiment, the luminescent material is a porphyrin derivative.

DETAILED DESCRIPTION OF THE INVENTION

Figure 1:
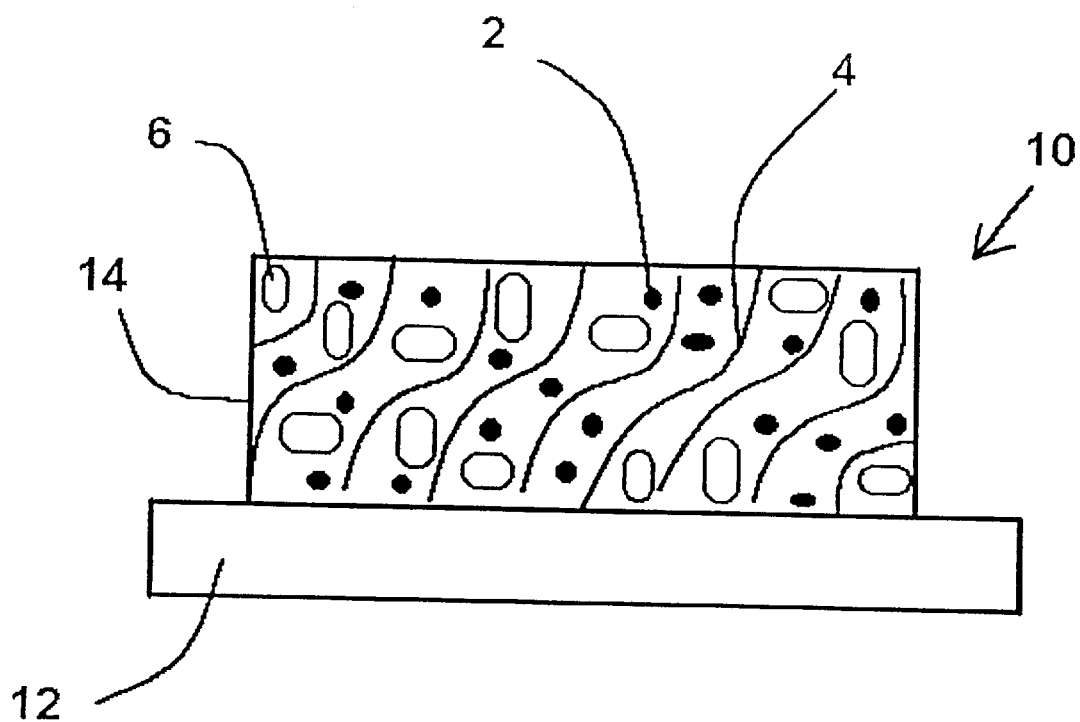
FIG. 1 illustrates an exemplary optical sensor in accordance with the present invention.

The invention is directed towards more predictably obtaining optical sensors comprising polymeric sensing formulations, for measuring $O_2$ levels in patient blood samples. These formulations may be deposited as a membrane on light-transmissive substrates, e.g., optically clear polymers such as MYLAR®, or glass. These formulations include a luminescent dye and a light-transmissive, oxygen-permeable matrix having a desired oxygen permeability ($Perm_{O2}$) which will provide a Stern-Volmer constant in a desired range for the polymeric sensor composition. The matrix material comprises at least a copolymer (or terpolymer, etc.) prepared from monomeric units from a first homopolymer having a first $Perm_{O2}$ value, and monomeric units from a second homopolymer which has a second $Perm_{O2}$ value, wherein the first and second $Perm_{O2}$ values bracket the desired $Perm_{O2}$ value, i.e., one is below and one is above the desired $Perm_{O2}$. By adjusting the relative amounts of the first and second monomeric units, a number of copolymers having $Perm_{O2}$ values (and, by extension, (for a given dye) oxygen sensing membranes having a range of Stern-Volmer characteristics ($k_{SV}$)) spanning the desired range may be obtained. In a desirable embodiment, a plot of $Perm_{O2}$ value v. monomeric unit ratios can be used to obtain, for a given $Perm_{O2}$, the homopolymer reactant ratio necessary to obtain that $Perm_{O2}$.

"Homopolymer" as used herein, refers to a polymer made up of a single basic repeating monomeric unit. "Copolymer" refers to a polymer made up of at least two different basic subunits or monomeric species. "Copolymers" include, without limitation, alternating copolymers, random copolymers, statistical copolymers, block copolymers, graft copolymers, linear copolymers, branched copolymers (including star copolymers, graft copolymers, comb copolymers, ladder copolymers and semi-ladder copolymers) and network copolymers (i.e., cross-linked copolymers). The incorporation of additional monomeric units (i.e., to form heteropolymers), functional groups, etc., is contemplated and intended to be within the scope of the present invention. A "heteropolymer" is a polymer chain constructed from repeating subunits of three or more different monomeric unit species.

"Polymeric sensing membrane", as used herein, refers to articles such as membranes or thin detection layers made of a composition which exhibits the quenching of luminescent energy by a gas such as $O_2$, and can be used for quantitative and qualitative determination of the gas concentration in the environment being measured. The sensing membranes comprise a polymeric material containing at least one luminescent dye species preferably well-dispersed in the polymeric material.

"Luminescence", as used herein, means light emitted from a molecule by radiative dissipation of energy from an electronically excited state. "Fluorescence", as used herein, means luminescence resulting from the transition between states of identical multiplicity, typically between the lowest excited singlet state and the singlet ground state of the molecule. "Phosphorescence", as used herein, means luminescence resulting from the transition between states of differing multiplicity, typically between the lowest excited triplet state and the singlet ground state.

The homopolymers which comprise the monomeric units from which the copolymers of the disclosure are made may be prepared from ethylenically polymerizable monomeric units, such as detailed in the Examples herein. The same method used to prepare the homopolymers, may, therefore, be used to prepare the copolymeric light transmissive matrices described herein as well. In the development of this invention, it has been found that the oxygen permeability of the copolymeric matrix obtained from the procedures disclosed herein is made easier through the construction of a curve plotting the oxygen permeability obtained from polymers prepared with varying ratios of first and second monomeric units. From this curve a homopolymer reactant ratio may be obtained for a given oxygen permeability.

The copolymers constituting the oxygen permeable matrices of this disclosure are typically prepared by simple or random copolymerization of the first and second monomeric units, using techniques known to those in the art. This method has the benefit of simplicity, and insures that the essential component properties are blended into the resulting copolymer matrix material. However, as noted above, variations on this procedure may be incorporated. For example, a graft copolymer made by, say, grafting short homopolymer chains made from a first monomeric unit onto a backbone formed from polymerization of the second monomeric unit may be obtained as well. It is recognized that the properties of such a material, i.e., oxygen permeability, may likely be different from a copolymer incorporating the same reactant ratio but prepared in a different fashion (such as the random polymerization process disclosed above.) However, such variations are contemplated to be within the scope of this invention. Specific methods for obtaining the copolymers which form the oxygen permeable matrix of this invention are disclosed in the various examples appended to this disclosure, and are not intended to limit the invention, but simply illustrate that commonly used methods known in the art for preparing copolymers may be used. So as to better enable deposition of the light transmissive, oxygen permeable matrix, by methods such as spin casting, the resulting copolymer is desirably soluble in organic solvents such as tetrahydrofuran (THF).

Examples of homopolymers containing monomeric units from which the copolymers of the disclosure may be prepared include poly(amides), poly(acrylamides), poly (acrylates), poly(alkylacrylates), poly(styrenes), poly (nitriles), poly(vinyl chlorides), poly(vinyl alcohols), poly (dienes), poly(esters), poly(carbonates), poly(siloxanes), poly(urethanes), poly(olefins), poly(imides), and cellulosics.

If the ratio of luminescent dye molecules to polymeric material in a polymeric sensing membrane is too high, the dye molecules may coalesce, resulting in a decrease in gas permeability through the membrane and giving rise to non-ideal behavior. Desirably, the polymeric sensing membrane should comprise no more than about 4 wt % luminescent dye, more desirably no more than about 2 wt % luminescent dye and most desirably no more than about 1 wt % luminescent dye.

Any luminescent dyes capable of excitation, quenchable emission by the gas to be sensed, and dispersion within a light-transmissive polymeric matrix as disclosed herein, may be used. Such dye molecules for oxygen sensors include, for example, fluorescent pyrene dyes as disclosed in U.S. Pat. No. 4,003,707, or perylene dyes as disclosed in U.S. Pat. Nos. 4,476,870 and 5,462,879. Other dyes which may be used in the present invention include, but are not limited to, ruthenium complexes as disclosed in U.S. Pat. No. 5,030,420 and *Anal.Chem.* 63, 337 (1991); lanthanide complexes as cited in U.S. Pat. No. 4,861,727; and porphyrin derivatives as disclosed in U.S. Pat. No. 5,043,286; WO Application No. 95/10522; in *Biosensors and Bioelectronics* 7, 199 (1991); *Anal. Chem.* 67, 4112 (1995); and *J. Chem. Soc. Perkin Trans.* 2, 103 (1995). Luminescent dye molecules which may be used further include pyrene-butyric acid, perylene-dibutyrate, benzo-perylene, vinylbenzo-perylene, (4,7-diphenyl-1,1-phenanthroline)$_3$Ru(II), and ligand metal complexes of ruthenium (II), osmium (II), iridium (III), rhodium (III) and chromium (III) ions with 2,2'-bipyridine, 1,10-phenanthroline, 4,7-diphenyl-(1,20-phenanthroline), 4,7-dimethyl-1,10-phenanthroline, 4,7-disulfonated-diphenyl-1,10-phenanthroline, 5-bromo-1,10-phenanthroline, 5-chloro-1,10-phenanthroline, 2-2'bi-2-thiazoline, 2,2'-bithiazole, or other a-diimine ligands and tetrabenzo-Pt-porphyrin, tetraphenyl-Pt-porphyrin, octaethyl-Pt-porphyrin, octaethyl-Pt-porphyrin ketone, octaethyl-Pt-chlorin, tetraphenyl-Pt-chlorin and other porphyrin derivatives.

Selection of a particular luminescent dye molecule will depend, at least in part, upon certain photo-physical properties of the luminescent dye molecule. Table 1 provides a comparison of some of these properties for selected dyes. The dyes themselves, except for octaethyl-Pt-porphyrin ketone, were supplied by the Central Research Laboratories of Ciba-Geigy Ltd in Basel, Switzerland and prepared as set forth in EP-A 97/03915. Octaethyl-Pt-porphyrin ketone was purchased from the Joanneum Research Institute in Graz, Austria. In many instances, it is advantageous to use a luminescent dye molecule that has a high quantum yield, i.e., one that emits a relatively high percentage of the radiation which the molecule absorbs. "Quantum yield", as used herein, denotes the ratio between the number of photons which are absorbed by a dye molecule to cause an electron within the dye molecule to undergo a transition from the ground state to an excited state and the number of photons which are emitted by the same dye molecule upon the return of the electron to the ground state from the excited state. A luminescent dye should preferably have a quantum yield of at least approximately 0.1, more preferably at least approximately 0.25, and most preferably at least approximately 0.5.

TABLE I

| DYE | (dPP)$_3$Ru | OEC | OEP | OEPK | TBP | TCHPP | mTPTBP |
|---|---|---|---|---|---|---|---|
| Excitation λ(nm) | 460 | 596 | 535 | 592 | 600 | 536 | 615 |
| ε$_λ$(L · mol$^{-1}$ cm$^{-1}$) | 30,000 | 69,000 | 55,400 | 55,100 | 20,900 | 54,900 | 88,100 |
| Emission λ (nm) | 600 | 780 | 650 | 756 | 760 | 651 | 773 |
| Em Φ$_o$ | 0.5 | 0.05 | 0.38 | 0.12 | 0.2 | 0.42 | 0.19 |
| Φ$_o$/Φ$_{air}$ | — | >70 | 400 | — | 50 | 380 | 47 |
| τ$_o$ (μsec) @ 23° C. (solvent) | 5.9 | 45 | 100 | — | 40 | 78 | 38 |
| τ$_o$ (μsec) polystyrene | 11.4 | 40 | 85 | 66 | 63 | 88 | 54 |
| ε$_λ$* Φ$_o$/1000 | 15.0 | 3.45 | 21.1 | 6.61 | 4.18 | 23.0 | 16.7 |
| LED | Blue | Orange | Green | Yellow | Orange | Green | Orange |
| λ (nm) | 450 | 605 | 555 | 580 | 612 | 555 | 612 |

Abbreviations:
(dPP)$_3$Ru: (4,7 diphenyl-1,1-phenanthroline)$_3$ RuII
OEC: octaethyl-Pt-chlorin
OEP: octaethyl-Pt-porphyrin
OEPK: octaethyl-Pt-porphyrin ketone
TBP: tetrabenzo-Pt-porphyrin
TCHPP: tetracyclohexenyl-meso-tetraphenyl-Pt-porphyrin
mTPTBP: meso-tetraphenyl-tetrabenzo-Pt-porphyrin Ideally, a luminescent dye molecule should also absorb a relatively high amount of the radiation to which the dye molecule is exposed. This property may be measured by the extinction coefficient at a wavelength of peak light absorbance. The term "extinction coefficient" as used herein refers to the absorbance of light by a one molar solution having a pathlength of 1 cm. A luminescent dye molecule preferably has an extinction coefficient of at least approximately 20,000 L/mol-cm, more preferably at least approximately 50,000 L/mol-cm, and most preferably at least approximately 75,000 L/mol-cm.

As is known in the art, neither the quantum yield nor the extinction coefficient alone are sufficient indicators of the efficiency with which a luminescent dye molecule converts incident radiation to luminescence. However, the product of the quantum yield and the extinction coefficient can be used as a guide in determining a dye molecule's efficiency in converting the incident radiation to luminescence for a given sensing system.

To decrease the cost of using polymeric sensing membranes, it is often desirable to use a luminescent dye molecule for which excitation, detection of luminescence and processing of signal information can be carried out using relatively simple electronic components. Readily available excitation sources which may be used herein include flashlamps, tungsten halogen lamps, light emitting diodes (LEDs), lasers and laser diodes. LEDs are particularly desirable because they provide an inexpensive, low power consumption source of radiation. However, LEDs output relatively narrow bands of radiation; therefore, for a given luminescent dye molecule/LED combination, the absorbance wavelength of the dye molecule should approximately match the peak output wavelength of the LED. To optimize the sensitivity of a given polymeric sensing membrane, the emission spectrum of the fluorescent dye molecule dispersed within the membrane desirably should also be compatible with the peak sensitivity of a chosen detector. While short wave emission from pyrene and perylene dyes (approximately 400 nm to 500 nm) is detectable with most photomultiplier tubes, lower cost solid state detection circuitry is often advantageous for detecting emission at comparatively longer wavelengths of approximately 600 nm to approximately 1000 nm, e.g., photodiodes may be used for porphyrin dye-based membranes with an emission peaks in the range of 650 nm to 780 nm.

The response time requirement of the electronic instrumentation used to measure the decay time of a polymeric sensing membrane depends upon the emission lifetime of the luminescent dye molecules dispersed within the membrane. Table 1 shows that the lifetime ($\tau_o$) for a dye measured in solution is similar to that of the same dye dispersed within a single standard polymeric material of styrene. The experimental data for luminescent dyes in solution can thus be used to at least approximate the luminescent lifetime behavior of the same dye dispersed within a polymer. Longer unquenched ($\tau_o$) and quenched ($\tau$) luminescence lifetimes lower the frequency response necessary for detection and signal processing. This generally allows slower, more readily available and less expensive electronic equipment to be used when performing a measurement. For example, a polymeric sensing membrane including a ruthenium diphenylphenathroline dye having a $\tau_o$ of between 6 to 11.4 $\mu$sec would require instrumentation operating at a minimum frequency range of approximately 27 kHz to approximately 270 kHz. In contrast, a polymeric sensing membrane including octaethyl-Pt-porphyrin (OEP) having a $\tau_o$=85 $\mu$sec could operate in a minimum frequency range from approximately 2 kHz to approximately 20 kHz.

Particularly good dyes include meso-tetraphenyl-tetrabenzo-Pt-porphyrin (mTPTBP), tetracyclohexenyl-meso-tetraphenyl-Pt-porphyrin (TCHPP) and octaethyl-Pt-porphyrin (OEP); and mixtures thereof. As shown in Table 1, mTPTBP has a relatively long relaxation time $\tau_0$ of tens of microseconds, making it suitable for use with instrumentation having a response in the kHz range. The quantum yield Em$\Phi_o$ of 0.2 is reasonably strong, as is the absorbance-based extinction coefficient $\epsilon_\lambda$ of 88,100 L·mol$^{-1}$ cm$^{-1}$. The product of Em$\Phi_o$ and $\epsilon_\lambda$ for mTPTBP yields a relative figure of merit for optical signal generation $\epsilon_\lambda *\Phi_o/1000$, which is second only to octaethyl-Pt-porphyrin (OEP) and tetacyclohexenyl-meso-tetraphenyl-Pt-porphyrin (TCHPP). However, mTPTBP is also desirably more soluble in THF, compared to, e.g., TCHPP. The excitation or absorbance maximum at 615 nm for mTPTBP is also advantageous, since inexpensive, high output LEDs may be used to excite the dye, while the emission peak, near 775 nm, is ideal for peak sensitivity of silicon-based detectors.

Development of thin polymer coatings in accordance with the invention on a transmissive substrate has shown that it is possible to bring a sensitive luminescent coating into contact with samples while permitting both the excitation light and the emission signal to be transmitted through a transparent substrate from the "back" side of the sensor. These new coatings, which are typically thin, show an extremely rapid response (achieving>90% of the steady state value in less than one second) to step changes in $O_2$ levels. The coating/membrane thickness is desirably between ≈1 to 5 $\mu$m, desirably ≤about 3 $\mu$m, more desirably ≤about 2 $\mu$m, and more desirably ≤about1 $\mu$m. These sensors are robust, are capable of thousands of measurements over periods of days, and may be used with simple LED light sources and solid state detector circuitry.

In a simple luminescence amplitude-based system, there can be a fairly large fraction of the excitation light, as much as 90–95%, which passes through the membrane and into the sample, where it may be absorbed, scattered or reflected back into the sensing layer. In addition, the luminescent signal emitted from the sensing layer may also be absorbed, scattered or reflected from the sample back into the detection optics. These two effects can combine to produce as much as a four-fold change in the luminescence signal between a perfectly absorbing and perfectly reflecting sample. Although the optical properties of typical samples usually do not vary to this great an extent (i.e., from complete absorption to complete reflection) and the membranes themselves may cause at least some light attenuation, they do offer a significant source of uncertainty for this type of luminescent sensor when measured in the amplitude mode. A solution to this latter problem is inclusion of a filler material, having light attenuation properties, added directly to the dye and polymer layer of an optical sensor. One can thus eliminate the requirements for more complex layering chemistries or fabrication steps in the sensor production process by directly adding a scattering or relectant material directly to the sensing layer. It should be noted that additions of such fillers when added in large quantities may somewhat alter membrane properties by virtue of a shift in the sensing matrix composition.

The $O_2$-sensing formulations described above may be used for phase modulation, relaxation, or frequency based modes of luminescence detection. However, for measurements involving luminescence amplitude or amplitude ratios, a scattering filler material (as described in our co-pending and commonly-owned U.S. patent application Ser. No. 09/009,917, of even filing date, the entire disclosure of which is incorporated herein by reference) is desirably incorporated to prevent the influence of changes in the sample absorbance and reflectance characteristics. Accordingly, particles of, e.g., $TiO_2$ (such as TI-PURE® dry grade R-700 from E. I. du Pont de Nemours (Wilmington Del.)) may be added in amounts of up to 50 wt % (based on the total weight of the $O_2$-sensing membrane composition) to prevent light attenuation differences among blood and aqueous samples.

Optical sensors including the polymeric sensing membranes disclosed herein according to the present invention may include a substrate onto which the polymeric sensing material is deposited. The substrates are desirably light-transmissive materials. "Light-transmissive materials", as used herein, refers to materials preferably transmitting at least about 95% of electromagnetic radiation used to induce electronic excitations in luminescent material which result in emissions, more preferably at least about 98% as measured by the transmission mode.

Substrates appropriate for use in the present invention preferably have a permeability of at most about 0.05 Barrers, more preferably at most about 0.005 Barrers, and most preferably at most about 0.0005 Barrers, as measured by the methods disclosed in *J. Membrane Sci.* 9, 53 (1981). An exemplary and nonlimiting list of suitable substrates includes MYLAR®; polyethyleneterephthalate (PET); SARAN®; ACLAR® and glass. Other suitable materials will be apparent to those of ordinary skill in the art and are intended to be within the scope of the present invention.

Gas permeability is defined herein as the volume of gas (at standard temperature and pressure) that flows per unit time, multiplied by the thickness of the material, and divided by the area of the material and the pressure differential across the material in that area. Conversion to the Barrer unit standard:

$$(([cm^3] \times thickness[cm]) \times 10^{-10})/(area[cm^2] \times time[sec] \times P_{diff}[cm\ Hg]),$$

may-be accomplished by standard conversion constants such as disclosed in the *Polymer Handbook,* third edition, John Wiley & Sons, New York, N.Y., (1989). Another approach to measuring gas permeability is disclosed in *J. Polym. Sci.* 41, 1 (1973). Other methods of measuring the permeability are known to those skilled in the art and are intended to be within the scope of the present invention.

In certain cases, the water uptake characteristics of a polymeric material may be important, since $O_2$ permeability of the membrane can change if the polymeric sensing membrane is exposed to water or water vapor and becomes hydrated. Membrane hydration can also cause the luminescence lifetime of a dye molecule dispersed within the membrane to change, through dipole effects on the ground and excited state transitions. Therefore, in embodiments where the polymeric sensing membrane is exposed to water or water vapor, the water uptake characteristics of the membrane should be such that the gas permeability and subsequently the luminescence lifetime are resistant to hydration over the course of the intended use. For example, the polymeric material should have relatively low or slow water uptake (so that the membrane does not become substantially hydrated over the course of an experiment). Relatively high or fast water uptake may be permissible in some cases, however, only where the membrane is substantially hydrated before measurements even occur and the water dipole does not adversely influence the dye properties.

The flexibility of a polymeric sensing membrane depends upon the flexibility of the polymer included in the membrane. For some uses, it may be desirable for a polymeric sensing membrane to be relatively flexible. Such flexibility would allow the membrane to conform to nonuniformities between mating surfaces. In addition, a flexible membrane may preclude the use of a sealing gasket in some sensor chamber constructions. Furthermore, a flexible membrane is less likely to delaminate from a flexible substrate layer than a brittle membrane would. Typically, the flexibility of a polymeric sensing membrane is related to the glass transition temperature ($T_g$) of the polymeric material. Since many of the physical properties of polymeric materials, including gas permeability, change at or near the glass transition temperature, polymer sensing membranes should not have a $T_g$ too close to the intended operation temperature. For example, membranes for $O_2$ determination in whole blood samples at 37° C. should not have a glass transition temperature near 37° C. Accordingly, $T_g$ in such cases is desirably nearer the extremes between about −40° C. and approximately 110° C.

Referring to the Drawings, FIG. 1 depicts a sensor 10 which comprises a sensing membrane or detection layer 14 on a transparent substrate or support 12. Essential components of the sensing layer or membrane 14 are the luminescent material 2 or dye itself, and the polymer matrix or binder material 4. If optical isolation is also desired, as in the case of luminescence amplitude-based measurements, a reflective or scattering filler material 6 may also be added to the membranes.

Figure 2:
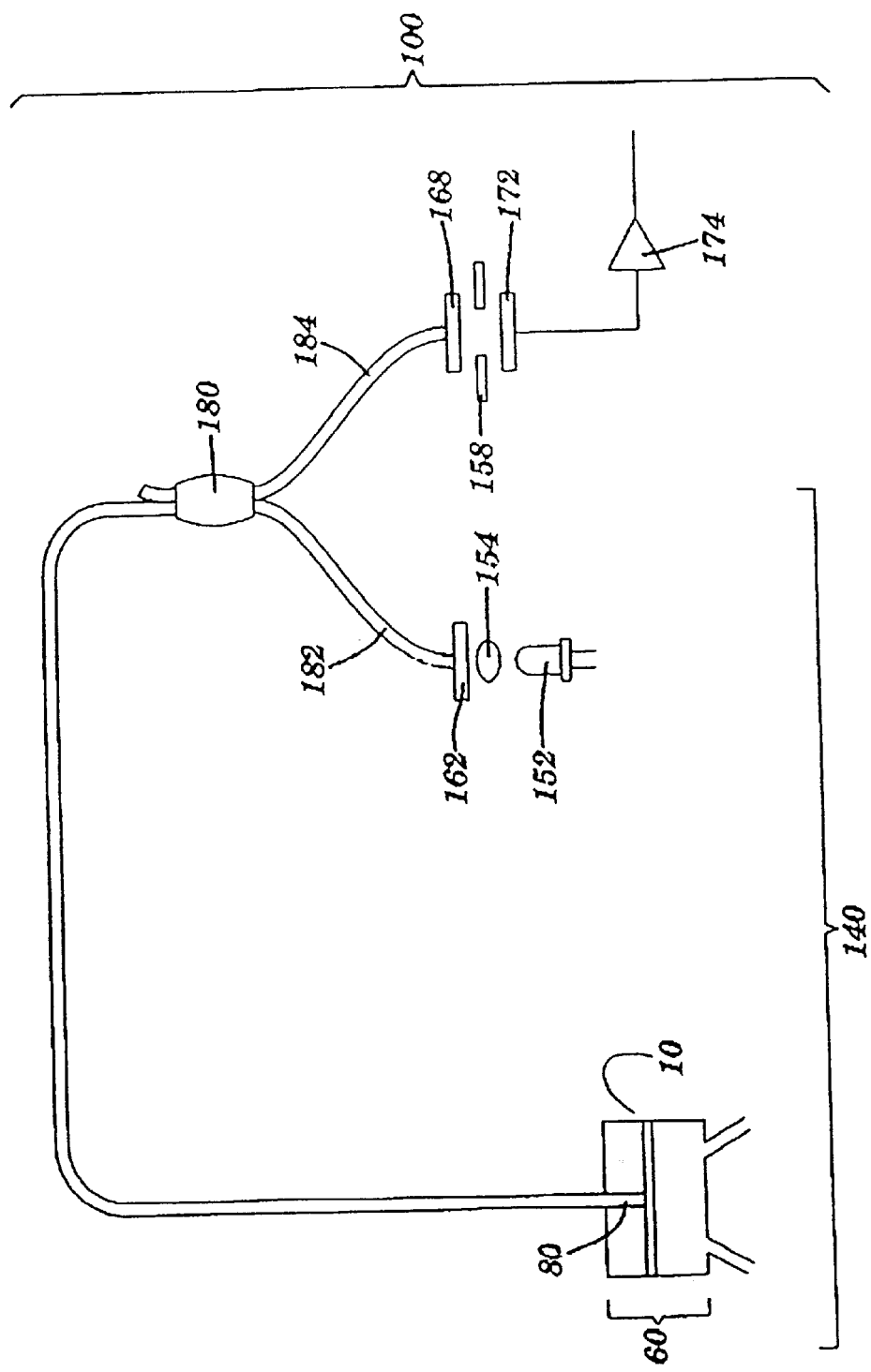
FIG. 2 is a schematic representation of a test apparatus for measuring an output signal amplitude of a luminescent optical sensor as described herein.

FIG. 2 describes a suitable device for measuring the luminescent amplitude response of optical sensors 10 in the present invention. The measurement apparatus 140 is comprised of a flow cell assembly 60 and a source and detector sub-system 100. For the optical source and detector sub-system 100, LED source 152 and lens 154 direct excitation light through filter 162 into one leg 182 of fiber optic splitter 180 (e.g., from American Laubscher Corp., Farmingdale, N.Y.). The luminescent light signal returning from the sensor 10 through fiber cable 80 and leg 184 is passed through filter 168 and aperture 158 before detection by photodiode 172 (e.g., from Hamamatsu Corporation, Bridgewater, N.J.). The output current of emission detector 172 is amplified with a preamplifier 174, such as a Stanford Research SR570 current preamplifier (Stanford Research Systems, Inc., Sunnyvale, Calif.), and converted to a voltage and recorded for use in analysis.

For example, with the dye meso-tetraphenyl-tetrabenzo-Pt-porphyrin (mTPTBP) a super bright orange LED (TLOH180P available from Marktech International Corp, Latham, N.Y.) may be used for source 152. An interference filter with a 580 nm center wavelength and 100 nm half bandwidth (e.g., from Omega Optical, Brattleboro, Vt.) may be used for filter 162 and a 710 EFLP long wavelength pass filter for emission above 710 nm (Omega Optical, Brattleboro, Vt.) was used for filter 168. Each individual sensor detection layer 14, employing a different dye as the luminescent material 2, will typically require its own preferred LED source 152, excitation filter 162 and emission filter 168.

When the luminescence detection layer 14 of optical sensor 10 is brought in contact with the sample by means of flow cell assembly 60, in order to measure the analyte gas, the optical emission signal that is generated and subsequently conveyed by fiber optic 80 to the excitation and detection sub-system 100 will be representative of the luminescent amplitude response. For frequency-based measurements one may employ the apparatus described in U.S. patent application Ser. No. 08/617,714.

Figure 3:
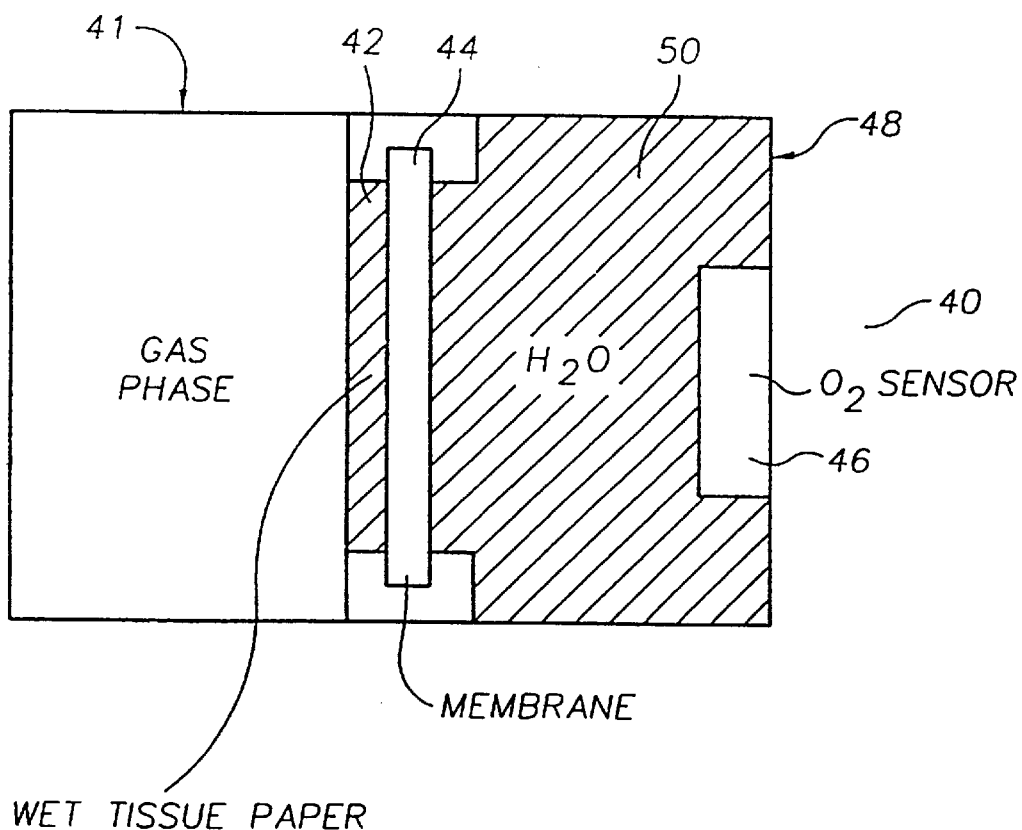
FIG. 3 is a schematic view of an apparatus suitable for measuring gas permeability of membranes as disclosed herein.

FIG. 3 depict s an apparatus 40 for measuring oxygen permeation using polymeric sensing membranes. In apparatus 40, a constant flow of gas containing a fixed concentration of oxygen passes through chamber 41 over a wetted tissue paper 42 on one side of the membrane 44. An oxygen sensor 46, such as a Clark electrode, monitors the rate of oxygen increase in a chamber 48 containing a stirred, fixed volume of water 50.

The following illustrative and nonlimiting examples are intended to demonstrate certain aspects of the present invention.

EXAMPLE 1

A copolymer made from the starting monomeric units 2-ethylhexylmethacrylate (20%) and methylmethacrylate (80%) was prepared as follows. The starting materials were all either recrystallized or freshly distilled to ensure purity. 22.07 g of 2-ethylhexylmethacrylate having a molecular weight (MW) of 184.28, 47.92 g of methylmethacrylate (MW=100.00), and 0.070 g of the initiator azo-bis-isobutyronitrile (MW=192.3) were dissolved to form a homogeneous solution. Two glass plates, each with a sealing rubber gasket along three edges, were mounted parallel to one another and separated by a space of about 2 mm. The form was then filled with about 32 g of the above solution and heated to 60° C. for 42 hours in a dry box flushed with nitrogen. The mixture was polymerized in a random fashion to a solid state, then dissolved in about 150 ml of chloroform, filtered through a glass filter, and precipitated into 4 liters of methanol. The precipitated polymer was then dried in a vacuum at 40° C. for 3 days. A membrane formed from this polymer had a measured permeability of 0.9 Barrers at 25° C.

EXAMPLE 2

To demonstrate the principle of constructing appropriate copolymers to give required performance properties, $O_2$-sensing membranes in accordance with the invention were formulated with OEP and a series of copolymers. The sensing membranes were formed on glass cover slips by spin casting solutions containing 2 mg of dye and 100 mg of polymer dissolved in 1 ml of THF. The copolymer series was constructed by selecting a relatively low permeability homopolymer (polymethylmethacrylate) and a higher permeability material polyethylhexylmethacrylate. The copolymers themselves were synthesized from the corresponding monomeric units methylmethacrylate (MMA) and ethylhexylmethacrylate (EHA) by the method in Example 1 and as disclosed in U.S. Pat. No. 5,387,329, the entire disclosure of which is incorporated herein by reference. As shown in Table II, the polymerization of MMA with increasing ratios of EHA produces polymers which, when mixed with the dye OEP, produce oxygen sensors with an increasingly sensitive response. This is evidenced by the increasing Stern-Volmer constant $k_{SV}$, measured at 25° C. Increasing the starting polymerization ratio from 0 mol % to 20 mol % EHA also increases the measured permeability seen in the fourth column. It is seen that by generating a copolymer systematically from materials of two different permeabilities one can tune the permeability to a value between permeabilities of the parent monomeric units and hence meet a specific performance criteria defined by the intermediate desired $k_{SV}$.

TABLE II

| Polymer | Monomers Mol %[1] | | Permeability (Barrers)[2] | $K_{sv} \times 10^3$ (mmHg)[3] |
| --- | --- | --- | --- | --- |
| | EHA | MMA | | |
| polymethylmethacrylate | 0 | 100 | 0.1 | 3.0 |
| EHA/MMA 5/95 | 5 | 95 | — | 8.0 |
| EHA/MMA 10/90 | 10 | 90 | — | 14.2 |
| EHA/MMA 15/85 | 15 | 85 | — | 22.0 |
| EHA/MMA 20/80 | 20 | 80 | 0.9 | 24.0 |

[1]Initial feed percentages for polymerization
[2]Permeabilities determined for selected polymers at 25° C.
[3]Stern-Volmer constant for luminescence quenching as a function of oxygen partial pressure determined at 25° C. with the dye octaethyl-Pt-porphyrin embedded in the copolymer designated.

EXAMPLE 3

The approach described in Example 2 was expanded using a different copolymer system. The monomeric units of the low permeability polyacrylonitrile ($Perm_{O2}$=0.0002 Barrers) and the more permeable polystyrene ($Perm_{O2}$=2.6 barrers) were chosen for copolymerization. As seen in Table III, increasing the mol % of the styrene component in the final copolymer from essentially zero to 100% increases the $k_{SV}$ observed. This rise in oxygen quenching ability parallels the rising permeability of the copolymers selected for comparison.

TABLE III

| Polymer | Monomers Mol %[1] | | Permeability | $K_{sv} \times 10^3$ (Barrers)[2] (mmHg)[3] |
| --- | --- | --- | --- | --- |
| | STY | AN | | |
| polyacrylonitrile | 0 | 100 | 0.0005 | <0.6 |
| STY/AN 10/90 | 10 | 90 | — | 3.0 |
| STY/AN 14/86 | 14 | 86 | 0.0042 | |
| STY/AN 20/80 | 20 | 80 | — | 4.6 |
| STY/AN 25/75 | 25 | 75 | — | 7.3 |
| STY/AN 34/66 | 34 | 66 | 0.048 | 9.3 |
| STY/AN 43/57 | 43 | 57 | 0.19 | 10.8 |
| STY/AN 58/42 | 58 | 42 | — | 16.0 |
| STY/AN 61/39 | 61 | 39 | 0.46 | — |
| STY/AN 66/34 | 66 | 34 | — | 18.8 |
| STY/AN 70/30 | 70 | 30 | — | 20.5 |
| STY/AN 80/20 | 80 | 20 | — | 27.0 |
| STY/AN 91/9 | 91 | 9 | — | 30.8 |
| polystyrene | 100 | 0 | 2.6 | 30.4 |

[1]Percentages based on Nitrogen content determined after polymerization.
[2]Permeabilities for oxygen determined for selected polymers at 25° C.
[3]Stern-Volmer constant for luminescence quenching as a function of oxygen partial pressure determined at 25° C. with the dye octaethyl-Pt-porphyrin embedded in the copolymer designated.

EXAMPLE 4

Figure 4:
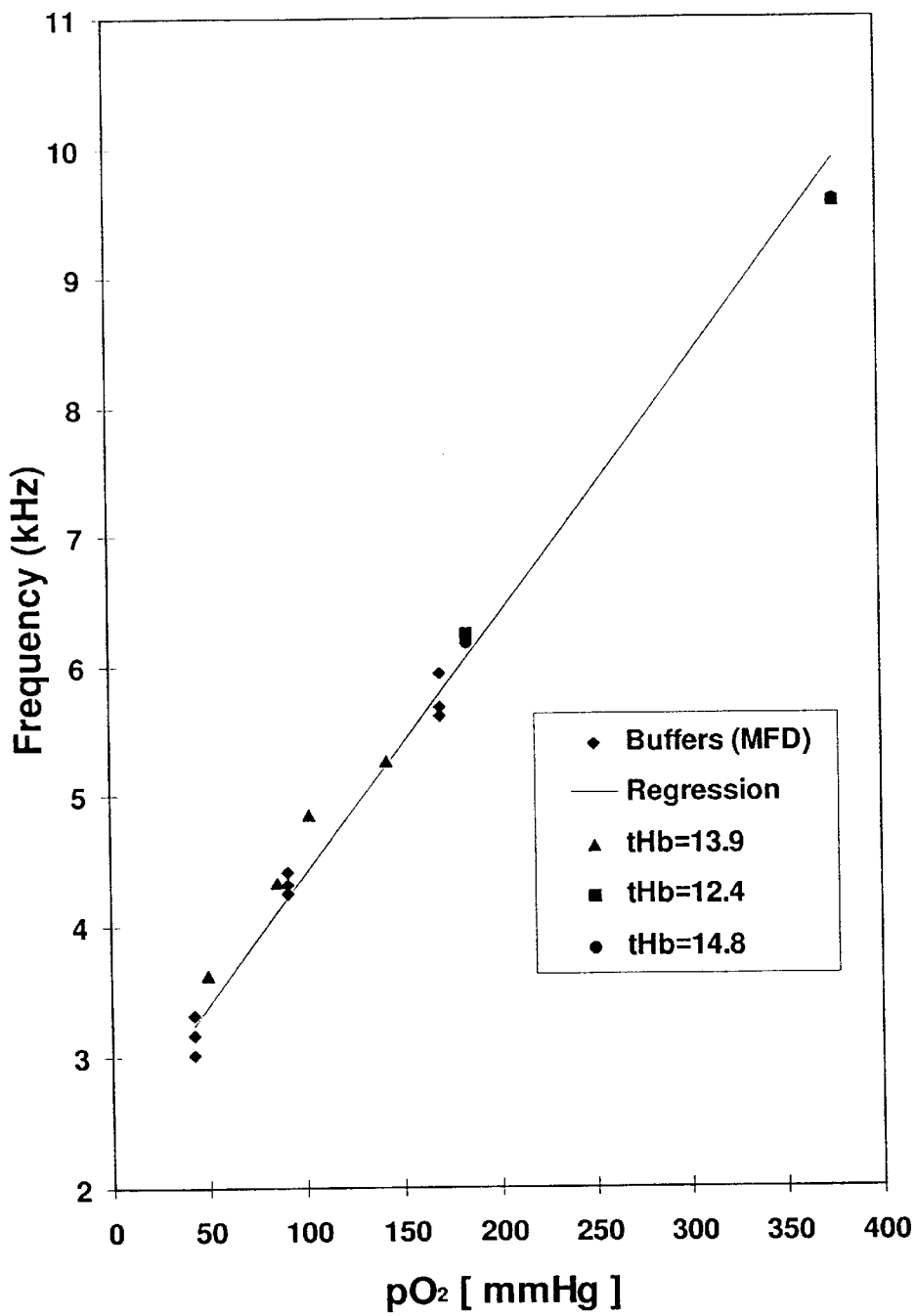
FIG. 4 is a graph depicting the frequency modulated response to oxygen of a membrane obtained in accordance with an embodiment of the invention comprising octaethyl-Pt-porphyrin dye (OEP) in a matrix of ethylhexylmethacrylate/methylmethacrylate copolymer (EHA/MMA 10/90)

The principle of sensing blood oxygen using the porphyrin dye OEP in a polymer whose permeability has been adjusted by copolymerizing ethylhexylmethacrylate and methylmethacrylate monomeric units in a ratio of 10/90, is illustrated in FIG. 4. A sensor formulation was prepared by dissolving 2 mg of OEP and 100 mg of the above copolymer in 1 ml of THF, followed by spin coating at 2000 RPM on a glass microscope slide. Tonometered liquid buffers (diamond symbols) were used to generate the calibration or regression line, while the other symbols represent tonometered blood values also obtained by the frequency modulation mode described earlier.

EXAMPLE 5

Figure 5:
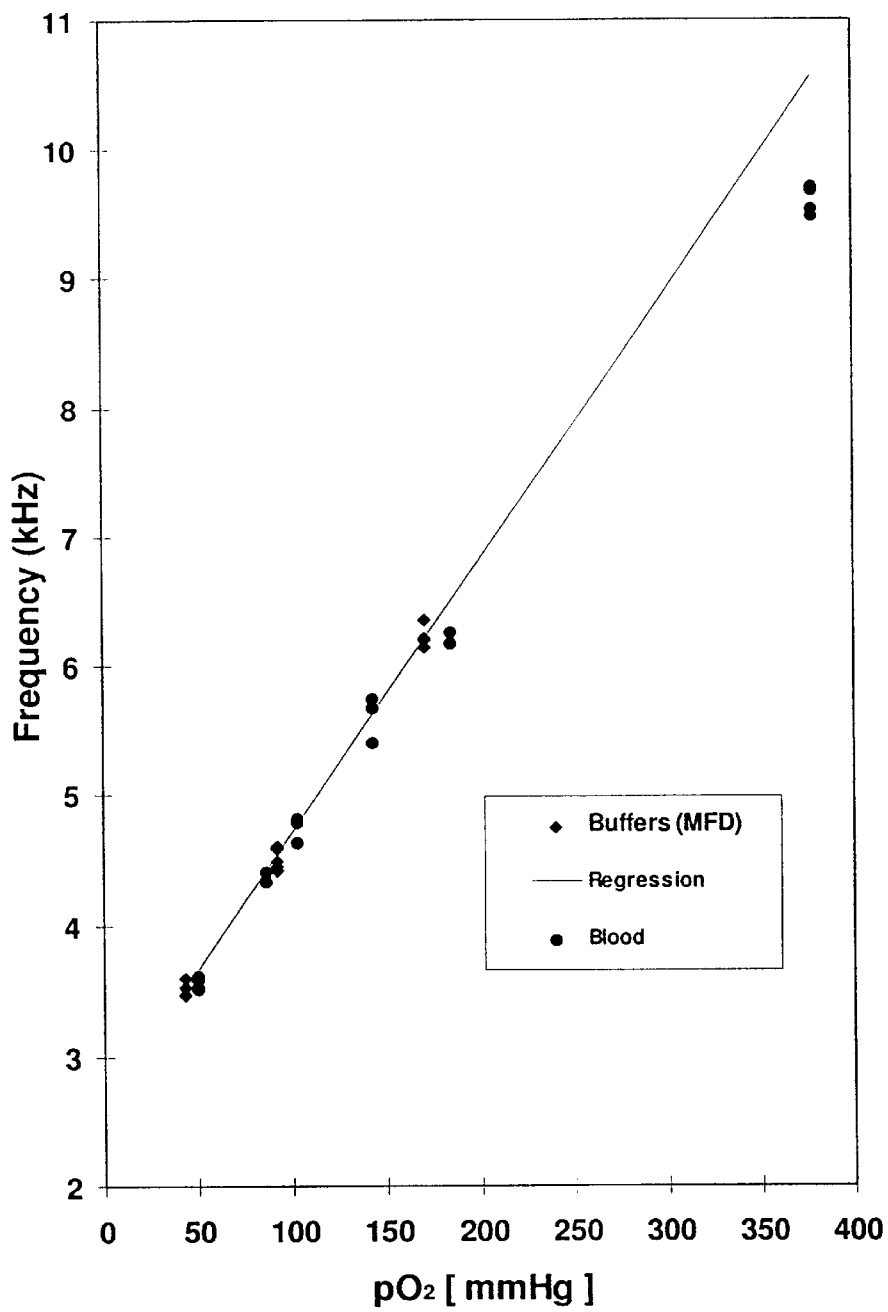
FIG. 5 is a graph illustrating the frequency modulated response to oxygen of a membrane obtained in accordance with an embodiment of the invention comprising OEP in a matrix of a styrene/acrylonitrile copolymer (STY/AN 58/42)

In FIG. 5, the dye OEP was alternately formulated with STY/AN 58/42 from the copolymer series developed from styrene and acrylonitrile. 2 mg of OEP and 100 mg of copolymer were dissolved in 1 ml of THF, then a thin sensor membrane was spin cast onto a clear MYLAR® substrate. As in FIG. 4, the blood values can be seen to follow a calibration curve of the frequency response to tonometered liquid buffers. In Table IV, oxygen levels determined by comparison of the individual blood measurements with the calibration line yield computed average values which are within the predetermined allowable error limits typically seen with commercial bloodgas instrumentation (e.g. a 278 series available from Chiron Diagnostics Corporation, Norwood, Mass.) with the exception of the highest oxygen value.

TABLE IV

STY/AN 58/42-OEP-MYLAR Blood Testing

| Tonometered mm $pO_2$ | Single Sensor Avg. Measured mm $pO_2$ | Calibration Error mm $pO_2$ | Allowable Error (+/−) mm $pO_2$ |
| --- | --- | --- | --- |
| 50 | 48.32 | −1.68 | 5.00 |
| 86 | 86.27 | 0.27 | 5.00 |

TABLE IV-continued

STY/AN 58/42-OEP-MYLAR Blood Testing

| Tonometered mm $pO_2$ | Single Sensor Avg. Measured mm $pO_2$ | Calibration Error mm $pO_2$ | Allowable Error (+/−) mm $pO_2$ |
|---|---|---|---|
| 103 | 103.87 | 0.87 | 5.15 |
| 143 | 144.04 | 1.04 | 7.15 |
| 185 | 172.46 | −12.54 | 18.50 |
| 378 | 330.60 | −47.40 | 37.80 |

EXAMPLE 6

Figure 6:
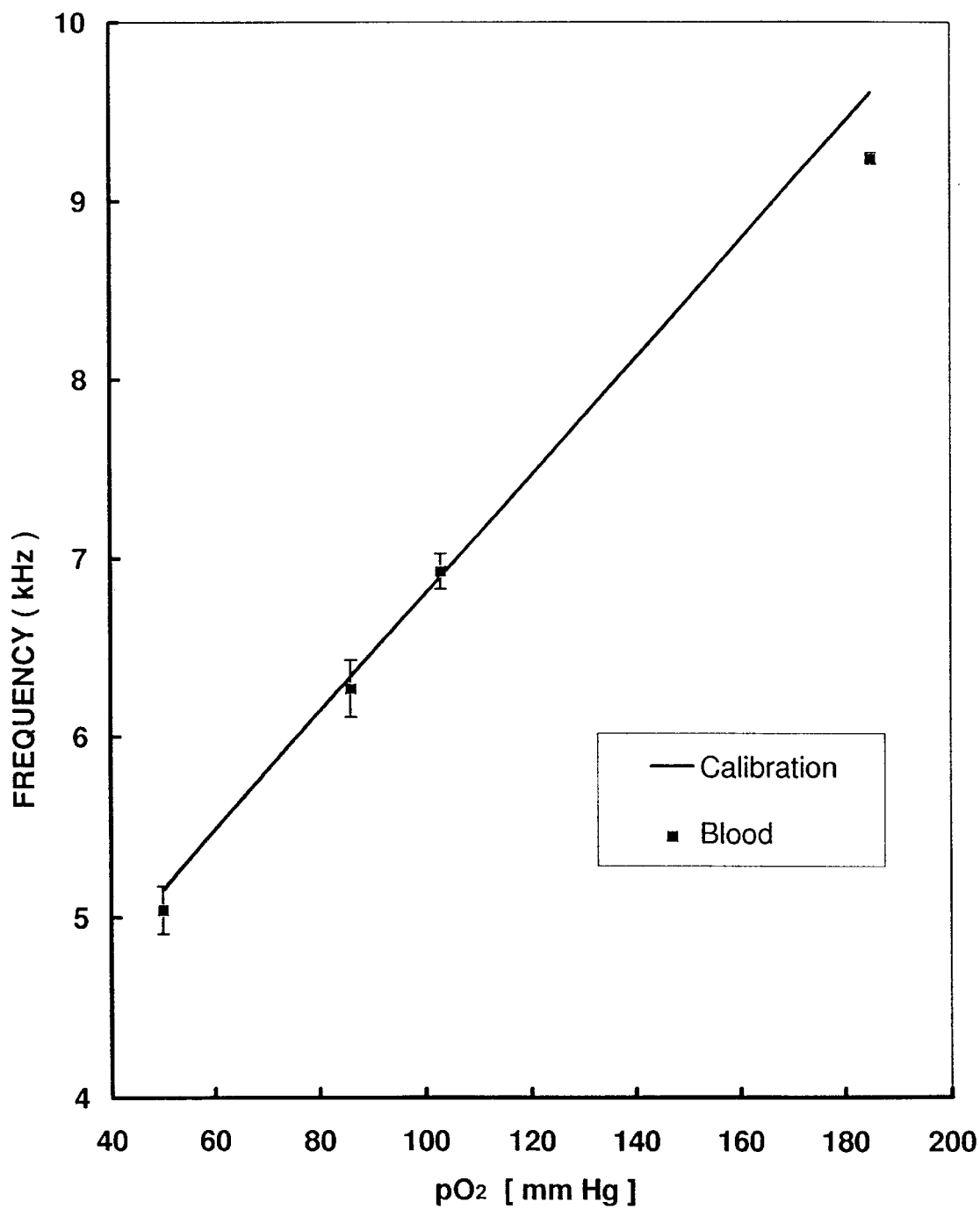
FIG. 6 is a graph showing the frequency modulated response to oxygen in blood samples of a membrane obtained in accordance with an embodiment of the invention comprising meso-tetraphenyltetrabenzyl-Pt-porphyrin dye (mTPTBP) in a matrix of a styrene/acrylonitrile copolymer (STY/AN 58/42)

FIG. 6 presents the data when mTPTBP dye was formulated with the styrene/acrylonitrile copolymer STY/AN 58/42. In this case, 2 mg of dye was dissolved with 100 mg of copolymer in 1 ml of THF and deposited by spin casting onto a glass substrate. After curing, replicate samples of tonometered blood were measured by the frequency modulation method and compared with the calibration line obtained from frequency measurements on tonometered aqueous buffer samples. As seen in Table V, oxygen levels determined by comparison of the individual frequency measurements with the calibration line yields computed average values which are also within the allowable error limits initially set as in Table IV.

TABLE V mTPTBP - STY/AN 58/42 Blood Testing

| Tonometered mm $pO_2$ | Avg. Measured mm $pO_2$ | Error mm $pO_2$ | Allowable Error (+/−) mm $pO_2$ |
|---|---|---|---|
| 50 | 46.67 | −3.33 | 5.00 |
| 86 | 83.92 | −2.08 | 5.00 |
| 103 | 103.91 | 0.91 | 5.15 |
| 185 | 173.88 | −11.12 | 18.50 |

EXAMPLE 7

Figure 7:
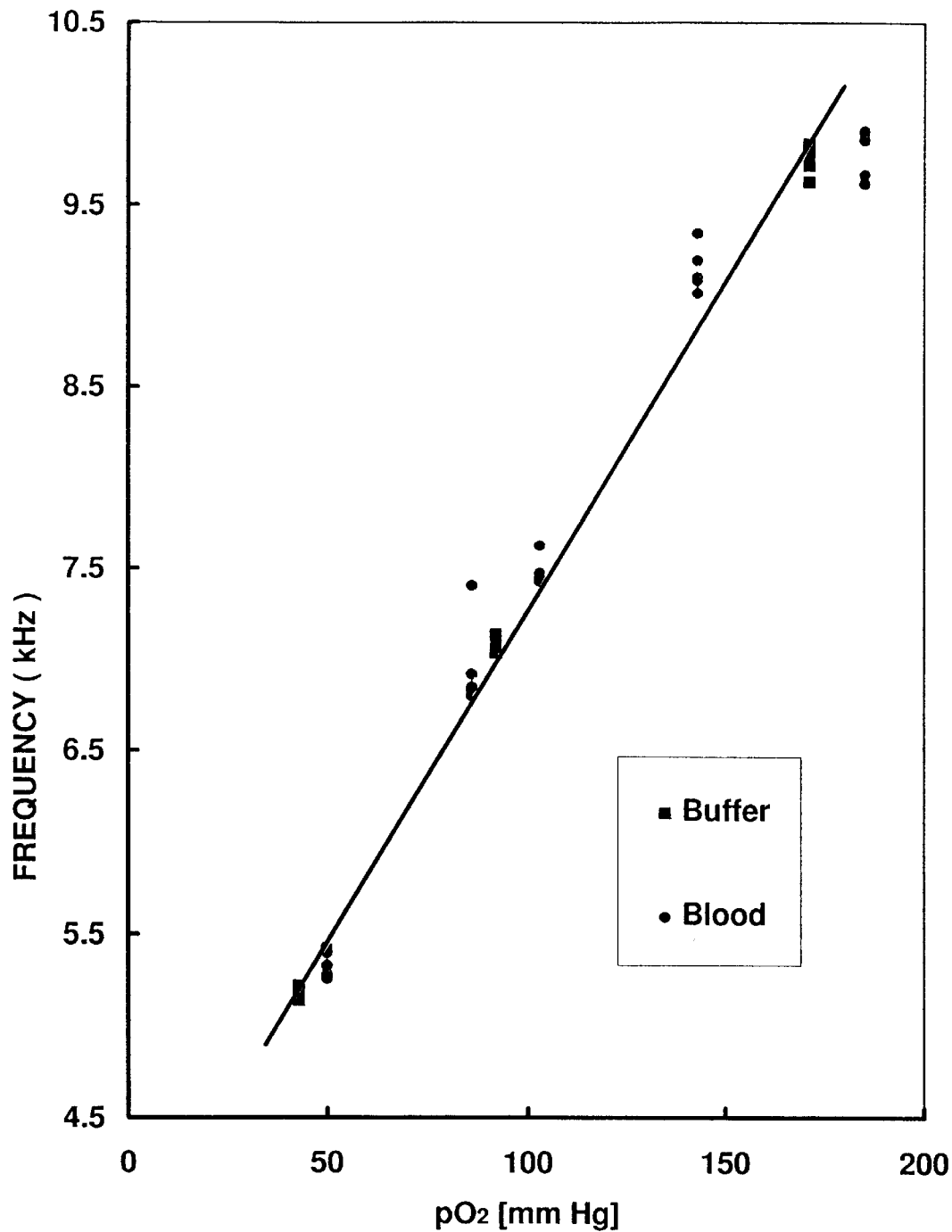
FIG. 7 is a graph depicting the frequency response to oxygen in blood samples of a membrane obtained in accordance with an embodiment of the invention comprising mTPTBP in a matrix of a ethylhexylmethacrylate/methylmethacrylate copolymer (EHA/MMA 15/85), as detailed in Example 7.

To demonstrate construction of a sensing membrane layer which may be used in commercial instrumentation, test stripes from a formulation containing mTPTBP and the copolymer EHA/MMA 15/85 from the ethylhexylmethacrylate/methylmethacrylate series were laid down using a continuous line deposition method (as described in our co-pending and commonly-owned U.S. patent application Ser. No. 09/010,096, the entire disclosure of which is incorporated herein by reference). The coating solution was made by adding 6 mg of mTPTBP, 300 mg of the ethylhexylmethacrylate copolymer EHA/MMA 15/85, and 3 ml THF to a glass scintillation vial and allowing the resulting mixture to dissolve overnight. Stripes of sensing material were deposited on a 75 µm thick clear MYLAR® film positioned with an IVEK LS Table (IVEK Corp., Springfield, Vt.). The mixture was deposited through a nozzle located 75 µm above a MYLAR® substrate at a rate of 5 µl/sec with a Digispense 2000 pump system from IVEK to produce a stripe at a linear rate of 50 mm/sec, having a width of approximately 2 mm and a thickness of about 5 µm when dried. After air drying, the stripes were cured at 110° C. for one hour under a vacuum and cooled to remove all traces of solvent. In FIG. 7 results are presented for stripes in which the dye mTPTBP is distributed within a copolymer EHA/MMA 15/85 sensing layer without the addition of a scattering filler material. In this case the excitation light from an orange LED at 612 nm was modulated at a frequency continuously adjusted to give a phase angle delay of 45°. The tonometered blood samples are seen to correspond well with the calibration line established by the use of tonometered aqueous buffers and obeying equation 8.

EXAMPLE 8

An oxygen sensor suitable for use in amplitude based luminescence measurements with intracoated sensor stripes (i.e., the polymeric sensing composition incorporates a reflective or scattering filler material), was made according to principles described in our copending and commonly-owned U.S. patent application No. 09/009,917, of even filing date, the entire disclosure of which is incorporated herein by reference. To prepare the stripes, coating solution was made in two steps. The first step was accomplished by adding 1 g EHA/MMA 15/85, 1 g $TiO_2$, 10 ml THF, and 10 tungsten beads to a glass jar and milling overnight. The second step was to add 6 mg of mTPTBP to 3 ml of the milled mixture followed by vortexing. Using the same conditions noted in Example 7, the stripes were laid down on MYLAR® from the milled and mixed coating solution.

Figure 8:
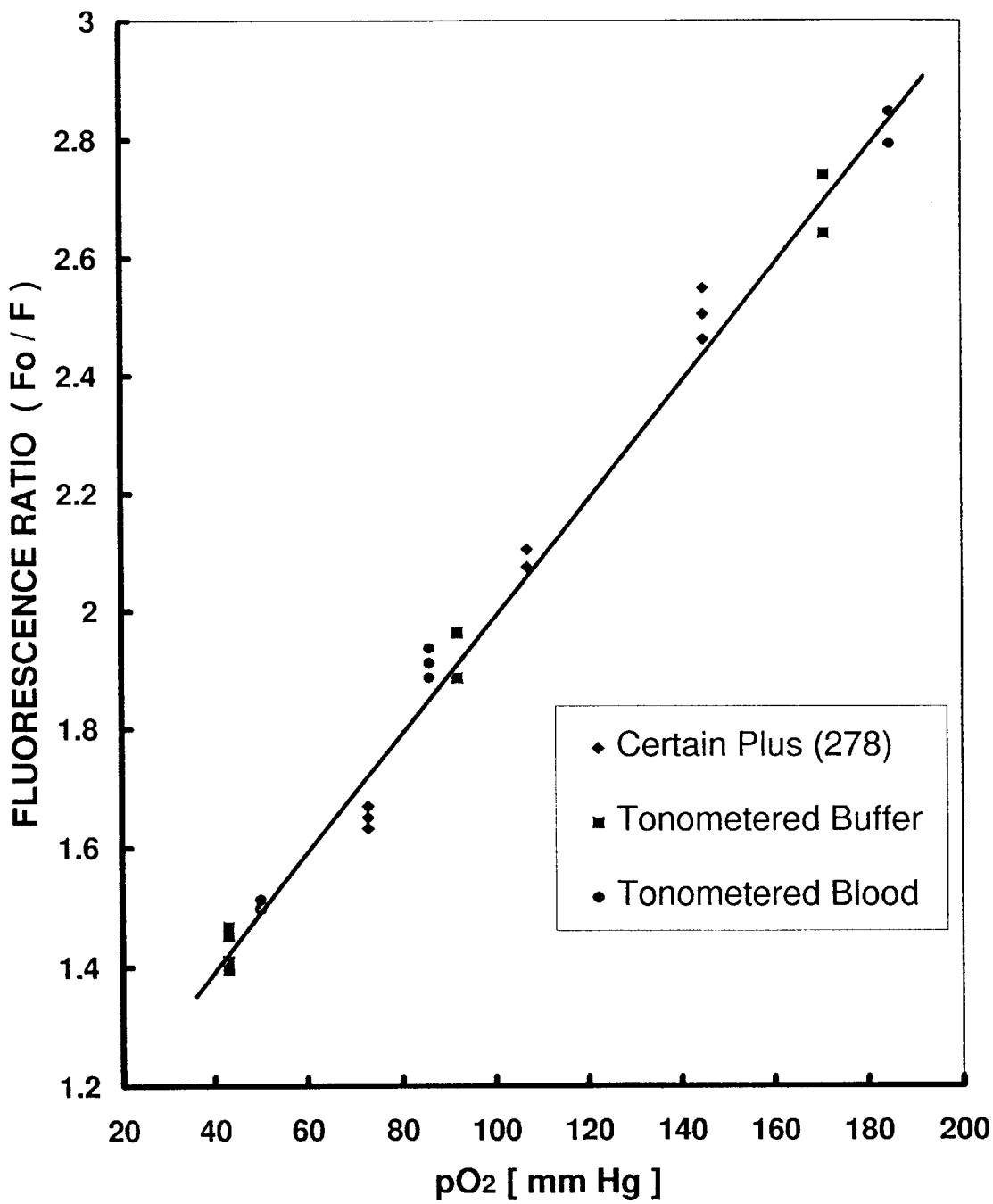
FIG. 8 depicts the luminescence amplitude based response ($F_o/F$) of tonometered blood samples as matching the Stern-Volmer relation derived for clear aqueous calibrants when membrane sensors further comprising $TiO_2$ particles (Example 8), are used.

The results of FIG. 8 show that tonometered blood samples also give a luminescence amplitude based response ($F_o/F$) matching the Stern-Volmer relation derived for clear aqueous sample calibrants when sensors containing the intracoating material are used. The points represent five separate sample values of either blood or liquid calibrants at each individual oxygen level.

EXAMPLE 9

The approach to tuning polymer permeability is not limited to only copolymers. A heteropolymer having desirable characteristics may also be modified by varying amounts of either the high or low permeability monomeric starting materials. One such example includes a polymer beginning with a starting material comprising 25% acrylonitrile, 10% 2-ethylhexylmethacrylate, 40% methylmethacrylate and 25% vinyl acetate and was synthesized as follows: 9.46 g acrylonitrile having a molecular weight of 53.06; 13.12 g 2-ethylhexylmethacrylate having a molecular weight of 184.28; 28.56 g methylmethacrylate having a molecular weight of 100.00; 15.33 g vinyl acetate having a molecular weight of 86.09 and 0.070 g of the initiator azo-bis-isobutyronitrile having a molecular weight of 192.3 were dissolved to form a solution. Two glass plates, each with a sealing rubber gasket along three edges, were mounted parallel to one another and separated by a space of 2 mm. The form was then filled with about 32 g of the above solution and heated to 60° C. for 42 hours in a dry box flushed with nitrogen. The mixture was polymerized to a solid state then dissolved in 150 ml of chloroform. It was subsequently filtered through a glass filter, and precipitated into 4 liters of methanol. The precipitated material was then dried in a vacuum for 3 days at 40° C. The membrane formed from this polymer, had a measured permeability of about 0.38 Barrers when measured at 23° C. 100 mg of the polymeric material and 2 mg of OEP were dissolved in 1 g of THF, and the solution was spin cast onto a glass substrate as in Example 2. The polymeric sensing membrane was cured in a vacuum oven for one hour at 65° C. The Stern-Volmer constant was calculated to be 0.0044 $(mmHg)^{-1}$ when measured at 23° C.

To adjust the response properties of the above polymer, the starting mole fraction of EHA was raised to 15% and the VAC fraction was dropped to 20%. When prepared by the above method this resulted in a similar heteropolymer which had a permeability to oxygen of 0.54 Barrers when cast polymer membranes were measured at 23° C. The Stern-Volmer constant was also correspondingly higher at 0.005 (mmHg)$^{-1}$ when measurements were similarly performed at 23° C.

Having thus described certain embodiments of the invention, various alterations, modifications and improvements will readily occur to those skilled in the art. Such alterations, modifications and improvements are intended to be part of this disclosure, and are intended to be within the spirit and scope of the invention. The materials employed, as well as their shapes and dimensions, may be altered. In addition, while the use of copolymeric sensing membranes in measuring oxygen concentration has been emphasized herein, it is to be understood that the present invention may be utilized in the measurement of the concentration of any gas so long as appropriate polymeric materials and luminescent dye materials as described herein can be designed and/or employed. Accordingly, the foregoing description is by way of example only and is not intended as limiting. The invention is limited only as defined in the following claims and the equivalents thereto.

What is claimed is:

1. A method of preparing a polymeric sensing composition containing a luminescent dye and a light transmissive, oxygen permeable matrix material, comprising the steps of:
   a. selecting a luminescent dye of incorporation in said polymeric sensing composition;
   b. determining a desired oxygen permeability (Perm$_{O2}$) range for said matrix material which will provide a Stern-Volmer constant in a desired range for said polymeric sensing composition; and
   c. preparing said light-transmissive, oxygen permeable matrix material having a glass transition temperature of approximately −40° C. or approximately 110° C. by
      i. selecting a first homopolymer comprised of first monomeric units said first homopolymer having a first Perm$_{O2}$ value;
      ii. selecting a second homopolymer having a second Perm$_{O2}$ value that is different than said first Perm$_{O2}$ value;
      iii. copolymerizing said first and second monomeric units to obtain a copolymer having an intermediate Perm$_{O2}$ values, said intermediate Perm$_{O2}$ sufficient to provide a Stern-Volmer constant within said desired range of Stern-Volmer constants;
      iv. incorporating said luminescent dye in said copolymer; and
      v. incorporating a scattering filler material in said copolymer.

2. The method of claim 1, wherein said step of incorporating a luminescent dye further comprises incorporating a luminescent dye selected from the group consisting of pyrenes, pyrelenes, ligand metal complexes of ruthenium, Pt chlorin derivatives and Pt-porphyrin derivatives.

3. The method of claim 1, wherein said step of incorporating a luminescent dye further comprises incorporating octaethyl-Pt porphyrin or meso-tetraphenyl-tetrabenzo-Pt-porphyrin.

4. The method of claim 1, wherein said preparing said light-transmissive, oxygen-permeable matrix material step further comprises selecting said homopolymers from the group consisting of poly(amides), poly(acrylamides), poly(styrenes), poly(acrylates), poly(alkylacrylates), poly(nitriles), poly(vinyl chlorides), poly(vinyl alcohols), poly(dienes), poly(esters), poly(carbonates), poly(siloxanes), poly(urethanes), poly(olefins), poly(imides), and cellulosics.

5. The method of claim 1, wherein said preparing said light-transmissive, oxygen-permeable matrix material step further comprises selecting said monomeric units from the group consisting of ethylhexylmethacrylate and methylmethacrylate.

6. The method of claim 1, wherein said preparing said light-transmissive, oxygen-permeable matrix material step further comprises selecting said monomeric units from the group consisting of styrene and acrylonitrile.

7. The method of claim 1 wherein said copolymerization of said first and second amounts of monomeric units results in a light-transmissive, oxygen-permeable matrix having a Perm$_{O2}$ value providing a k$_{SV}$ of at least $10 \times 10^{-3}$ at 37° C.

8. The method of claim 1, wherein said scattering filler material is selected from the group consisting of TiO$_2$, zinc oxide, antimony trioxide, barium sulfate, magnesium oxide, blush polymers, and mixtures thereof.

9. The method of claim 8, wherein said scattering filler material is TiO$_2$ or a blush polymer.

10. A method of preparing a light-transmissive, oxygen-permeable matrix material for use in a polymeric sensing composition, comprising the steps of:
    a. determining a desired oxygen permeability (Perm$_{O2}$) range for said matrix material which will provide a desired range of Stern-Volmer constants for said polymeric sensing composition;
    b. selecting a first homopolymer comprised of first monomeric units, said first homopolymer having a first Perm$_{O2}$ value;
    c. selecting a second homopolymer comprised of second monomeric units, said second homopolymer having a second Perm$_{O2}$ value that is different than said first Perm$_{O2}$ value; and
    d. preparing a copolymer having an intermediate Perm$_{O2}$ value between said first and second Perm$_{O2}$ values by copolymerizing said first and second monomeric units in a ratio to obtain said copolymer, said intermediate Perm$_{O2}$ value providing a Stern-Volmer constant within said desired range of Stern-Volmer constants wherein said copolymer contains a scattering filler material to form the polymeric sensing composition having a glass transition temperature of approximately −40° C. or approximately 110° C.

11. The method of claim 10, wherein a plurality of copolymers each having a separate intermediate Perm$_{O2}$ value between said first and second Perm$_{O2}$ values are prepared by copolymerizing said first and second monomeric units in a plurality of ratios to obtain said plurality of copolymers, said intermediate Perm$_{O2}$ values providing a plurality of Stern-Volmer constants within said desired range for said polymeric sensing compositions.

12. The method of claim 11, further comprising the step of selecting a light-transmissive, oxygen-permeable matrix material having a desired Perm$_{O2}$ value from said plurality of copolymers.

13. An oxygen sensor formulation comprising:
    a. a luminescent dye; and
    b. a light transmissive, oxygen permeable matrix material having a desired oxygen-permeability (Perm$_{O2}$) which provides a Stern-Volmer constant in a desired range for a polymeric sensing composition, made by the process of:
       i. selecting a first homopolymer comprised of first monomeric units, said first homopolymer having a first Perm$_{O2}$ value;
       ii. selecting a second homopolymer having a second Perm$_{O2}$ value that is different that said first Perm$_{O2}$ value;

iii. copolymerizing said first and second monomeric units to obtain a copolymer having a glass transition temperature of approximately −40° C. or approximately 110° C. and having an intermediate $Perm_{O2}$ value between said first and second $Perm_{O2}$ values, said intermediate $Perm_{O2}$ providing said desired Stem-Volmer constant in said range; and iv. including a scattering filler material in said copolymer.

14. The sensor formulation of claim 13 wherein said luminescent dye is selected from the group consisting of pyrenes, pyrelenes, ligand metal complexes of ruthenium, Pt-chlorin derivatives and Pt-porphyrin derivatives.

15. The sensor formulation of claim 14, wherein said luminescent dye is octaethyl-Pt porphyrin or meso-tetraphenyl-tetrabenzo-Pt-porphyrin.

16. The sensor formulation of claim 13 wherein said homopolymers are selected from the group consisting of poly(amides), poly(acrylamides), poly(styrenes), poly(acrylates), poly(alkylacrylates), poly(nitriles), poly(vinyl chlorides), poly(vinyl alcohols), poly(dienes), poly(esters), poly(carbonates), poly(siloxanes), poly(urethanes), poly(olefins), poly(imides), and cellulosics.

17. The sensor formulation of claim 16, wherein said monomeric units are selected from the group consisting of ethylhexylmethacrylate and methylmethacrylate.

18. The sensor formulation of claim 16, wherein said monomeric units are selected from the group consisting of styrene and acrylonitrile.

19. The sensor formulation of claim 13, wherein said scattering filler material is selected from the group consisting of $TiO_2$, zinc oxide, antimony trioxide, barium sulfate, magnesium oxide, and blush polymers, and mixtures thereof.

20. The sensor formulation of claim 19, wherein said scattering filler material is $TiO_2$ or a blush polymer.

21. The sensor formulation of claim 13, wherein said luminescent dye is octaethyl-Pt porphyrin and said monomeric units are ethylhexylmethacrylate in an amount of between about 5 to 15 mole percent of the total polymerizable monomer; and methylmethacrylate.

22. The sensor formulation of claim 21, wherein said amount of ethylhexylmethacrylate is about 10 mole percent of the total polymerizable monomer.

23. The sensor formulation of claim 13, wherein said luminescent dye is meso-tetraphenyl-tetrabenzo-Pt-porphyrin and said monomeric units are ethylhexylmethacrylate, in an amount of between about 10 to 20 mole percent of the total polymerizable monomer; and methylmethacrylate.

24. The sensor formulation of claim 23, wherein said amount of ethylhexylmethacrylate is about 15 mole percent of the total polymerizable monomer.

25. The sensor formulation of claim 13, wherein the luminescent dye is octaethyl-Pt porphyrin and said monomeric units are styrene, in an amount of between about 25 to 65 mole percent of the total composition of the copolymer; and acrylonitrile.

26. The sensor formulation of claim 25, wherein said styrene content is about 55 mole percent.

27. The sensor formulation of claim 13, wherein the luminescent dye is meso-tetraphenyl-tetrabenzo-Pt-porphyrin and said monomeric units are styrene, in an amount of between about 35 to 75 mole percent of the total composition of the copolymer; and acrylonitrile.

28. The sensor of claim 27, wherein said styrene content is 58 mole percent.

* * * * *